United States Patent [19]

Schmidt et al.

[11] Patent Number: 4,495,351
[45] Date of Patent: Jan. 22, 1985

[54] METHOD FOR THE PRODUCTION OF 1-ALKYL-6,7-METHYLENE-DIOXY-4(1H)-OXO-CINNOLIN-3-CARBOXYLIC ACIDS

[75] Inventors: Hans-Jörg Schmidt; Joachim Franke; Reingard Scheffler, all of Dresden; Heinz Tönjes; Günter Kammann, both of Radebeul; Günther Dietz, Dresden, all of German Democratic Rep.

[73] Assignee: Veb Arzneimittelwerk Dresden, Radebeul, German Democratic Rep.

[21] Appl. No.: 451,539

[22] Filed: Dec. 21, 1982

[30] Foreign Application Priority Data

Dec. 22, 1981 [DD] German Democratic Rep. .................... 2360676

[51] Int. Cl.$^3$ ................ C07D 491/056; C07D 317/66
[52] U.S. Cl. ..................... 544/234; 549/439
[58] Field of Search ............ 544/234, 235; 546/156, 546/123

[56] References Cited

U.S. PATENT DOCUMENTS

| | | | |
|---|---|---|---|
| 2,797,218 | 6/1957 | Barber et al. | 544/235 |
| 3,397,208 | 8/1968 | Berman et al. | 546/156 |
| 3,669,965 | 6/1972 | White | 424/250 |
| 4,264,604 | 4/1981 | Sturm | 546/156 |

FOREIGN PATENT DOCUMENTS 128703 8/1981 Japan .

OTHER PUBLICATIONS

Barber et al., J. Chem. Soc., 2828 (1961).
Ames et al., J. Chem. Soc., 5569 (1964).
Koga et al., J. Med. Chem., 23, 1358, (1980).

Primary Examiner—Donald G. Daus
Assistant Examiner—William A. Teoli, Jr.
Attorney, Agent, or Firm—Michael J. Striker

[57] ABSTRACT

A method is disclosed for production of 1-alkyl-4(1H)-oxo-cinnolin-3-carboxylic acids. Mesoxalic acid dialkylester-3,4-methylenedioxy-phenylhydrazone is saponified using 1 to 1.5 Mol alkali into the corresponding monoalkylester, which is cyclicized with a Friedel-Crafts catalyst in the presence of a carboxylic acid anhydride into 6,7-methylenedioxy-4(1H)-oxo-cinnolin-3-carboxylic acid alkylester, which is alkylated with a $C_1$-$C_4$ alkyl halogenide in the presence of alkali in a suitable solvent, after which the ester is saponified. Small amounts of byproduct alkylated in the 2-position are removed by brief heating and precipitation from alkaline solution, leaving a pure 1-alkyl product. The product is useful for the treatment of urinary tract infections.

15 Claims, No Drawings

METHOD FOR THE PRODUCTION OF 1-ALKYL-6,7-METHYLENE-DIOXY-4(1H)-OXO-CINNOLIN-3-CARBOXYLIC ACIDS

BACKGROUND OF THE INVENTION

The invention concerns a method for the production of 1-alkyl-6,7-methylenedioxy-4(1H)-oxo-cinnolin-3-carboxylic acids of the general Formula V

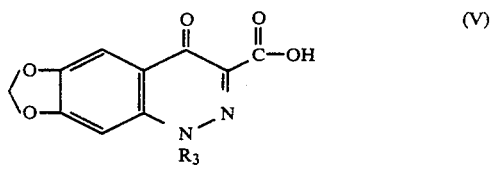

$R_1 =$ —$CH_3$; —$C_2H_5$; —$C_3H_7$; —$C_4H_9$
$R_2 =$ —$CH_3$; —$C_2H_5$; —$C_3H_7$; —$C_4H_9$
$R_3 =$ —$CH_3$; —$C_2H_5$; —$C_3H_7$; —$C_4H_9$ which are used as highly effective chemotherapeutics, particularly for the treatment of urinary tract infections.

The production of 1-alkyl-6,7-methylenedioxy-4(1H)-oxo-cinnolin-3-carboxylic acids is previously known only from DE-OS No. 2,005,104 corresponding to U.S. applications Ser. Nos. 796,546 and 888,880 and DE-OS No. 2,065,719. Accordingly, 4,5-methylenedioxy-2-amino-acetophenone is converted, through diazotization and heating, into 6,7-methylenedioxy-4(1H)-oxo-cinnolin, and through four further stages, bromination in the 3-position, exchange of bromine by cyano by means of CuCN, alkylation of the nitrile in the 1-position with alkyl halogenide and NaH, and subsequent saponification of the nitrile, made into carboxylic acid. The process possesses the disadvantage that proceeding from the 4,5-methylenedioxy-2-amino-acetophenone, the final compound is produced through five relatively expensive stages. On account of the extraordinarily great insolubility of the obtained intermediate compounds, the process must be performed at high temperatures using high-boiling solvents such as acetic acid and dimethylformamide.

Another method for the production of 6,7-methylenedioxy-4(1H)-oxo-cinnolin-3-carboxylic acid unsubstituted by nitrogen proceeds from o-nitropiperonal, which is condensed into the corresponding cinnamic acid derivative through condensation with malonic acid diethylester. Through bromination and subsequent HBr-splitting-off into o-nitropropiolic acid, reduction to amino group with subsequent diazotization and ring closure, the 6,7-methylenedioxy-4(1H)-oxo-cinnolin-3-carboxylic acid is obtained (J. Chem. Soc. 1945 512; 1949 2393). This synthesis is expensive and produces very low yields on account of the numerous side reactions, in particular with the cyclization of the diazotized o-aminopropiolic acid, and is therefore practically not utilized (T. L. Jacobs in Elderfield, Heterocyclic Compounds, 1977, Chapter 5, page 137).

4(1H)-oxo-cinnolin-3-carboxylic acid derivatives can moreover be produced through the corresponding phenylhydrazones of mesoxalic acid dichloride through cyclization with suitable Friedel-Crafts catalysts. The mesoxalic acid dichloride-phenylhydrazone is prepared from the corresponding aniline through diazotization and coupling with malonic acid ester, subsequent saponification of the mesoxalic acid diester-phenylhydrazone into the dicarboxylic acid and reaction with phosphorpentachloride or thionylchloride (H. J. Barber et al., J. Chem. Soc. 1961 2828, U.S. Pat. No. 2,797,218 of Aug. 2, 1954). As suitable catalysts particularly $TiCl_4$ and $SnCl_4$ are mentioned. Various substituents in the aromatic ring, in particular alkoxy groups, are, however, attacked through the catalysts, so that low yields are obtained or exclusively resinified products are produced.

The production of the acid chloride serving as starting product for the cyclization is unfavorable, on account of the aggressiveness of the reactants, and leads to a higher technical expenditure.

The solution of the problem according to the present invention was not foreseen; the attempts by Barber and collaborators to obtain a cyclization at the stage of the mesoxalic acid ester or mesoxalic acid-phenylhydrazone with catalysts such as $TiCl_4$, $SnCl_4$, $POCl_3$ or polyphosphoric acid, did not succeed (J. Chem. Soc. 1961 2828). Moreover, the N-alkylation of the 4(1H)-oxo-cinnolin-3-carboxylic acid with alkyl halogenide under basic conditions leads to mixtures of approximately the same portions of $N_1$ and $N_2$-substituted compounds, which, such as with the described 6-bromo-4(1H)-oxo-cinnolin-3-carboxylic acid, can be separated only with difficulty (D. E. Ames et al., J. Chem. Soc. 1964 5659; R. P. Brundage et al., J. Heteroc. Chem. 13 1085 (1976)).

SUMMARY OF THE INVENTION

It is therefore the object of the present invention to make available an economically favorable method for the production of 1-alkyl-6,7-methylenedioxy-4(1H)-oxo-cinnolin-3-carboxylic acids. In so doing, the deficiencies of the previously known technical solutions should be overcome.

Accordingly, it is an object of the present invention to find the conditions for cyclization of mesoxalic acid alkylester-3,4-methylenedioxy-phenylhydrazones into the corresponding 4-(1H)-oxo-cinnolin-3-carboxylic acid esters and their further reaction into the 1-alkyl-6,7-methylenedioxy-4(1H)-oxo-cinnolin-3-carboxylic acid esters, in good yield and higher purity.

At the same time, the number of reaction stages should be limited and the reaction conditions should be simplified.

It has now surprisingly been discovered that, proceeding from mesoxalic acid monoalkylester-3,4-methylenedioxyphenylhydrazone, which is prepared from 3,4-methylenedioxyaniline through diazotization and coupling with malonic acid dialkylester and saponification, with a suitable Friedel-Crafts catalyst, in particular a derivative of phosphoric acid, such as polyphosphoric acid, polyphosphoric acid ester of phosphoroxychloride, in the presence of a carboxylic acid anhydride, in particular acetic or propionic acid anhydride, at temperatures above 80° C., if necessary in the presence of a suitable solvent, to obtain 6,7-methylenedioxy-4(1H)-oxo-cinnolin-3-carboxylic acid alkylester. Through treatment with alkyl halogenide in the presence of alkali, if necessary under the addition of a phase transfer catalyst, 6,7-methylenedioxy-4(1H)-oxo-cinnolin-3-carboxylic acid alkylester is alkylated predominantly in the 1-position. Through subsequent saponification of the ester, the free acid is obtained.

For removal of the compound alkylated in the 2-position arising in small amounts, the product is briefly heated, in a suitable solvent, preferably dimethylformamide, preferably 2–10 minutes to 100° up to 150° C., preferably 120° C. With this reaction, the compound alkylated in the 2-position becomes exclusively decarboxylated. Through precipitation from alkaline solution, pure 1-alkyl-6,7-methylenedioxy-4-(1H)-oxo-cinnolin-3-carboxylic acid can be obtained.

The method has the advantage that, in comparison with the method described in J. Chem. Soc. 1961 2828, production of the mesoxalic acid dichloride derivative drops, and economically favorable catalysts, such as $POCl_3$, can be used for the cyclization. A further advantage is that the alkylation of the 6,7-methylenedioxy-4(1H)-oxo-cinnolin-3-carboxylic acid ester, in contrast to the free acid, proceeds to more than 80% in the desired 1-position, and, moreover, on account of the better solubility, the reaction can be performed in smaller amounts of solvent.

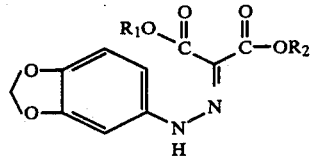

I

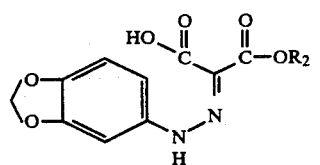

II

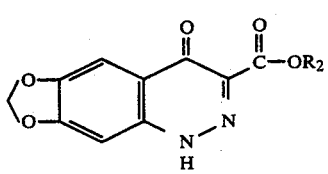

III

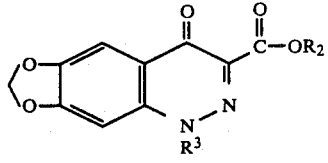

IV

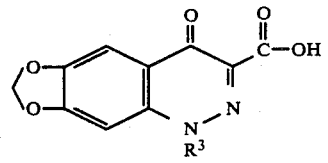

V

Wherein,
$R_1$ = $CH_3$; $-C_2H_5$; $-C_3H_7$; $-C_4H_9$
$R_2$ = $CH_3$; $-C_2H_5$; $-C_3H_7$; $-C_4H_9$
$R_3$ = $CH_3$; $-C_2H_5$; $-C_3H_7$; $-C_4H_9$ The novel features which are considered characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

EXAMPLE 1

In a 4 l flask with stirrer and thermometer, 347 g (2 Mol) 3,4-methylenedioxy-aniline-hydrochloride, 347 ml concentrated hydrochloric acid, 1 kg ice are provided, and the mixture is cooled to 0° C. Within 20 minutes, a solution of 150 g sodium nitrite in 400 ml water is added dropwise. The temperature is held to below +5° C. in connection therewith. In a 6 l sulfonation flask with stirrer and thermometer, 1.3 l ethanol, 1.2 l ice water, 402 g water-free sodium acetate and 303 g malonic acid diethylester are provided. The mixture is cooled to +5° C. and then, under stirring, the diazonium solution is added within 30 minutes. The cooling bath is removed and the mixture is stirred for another 2 hours at room temperature. Then, after several hours standing, the crystallisate is sucked off and washed with water.

Yield: 595 g mesoxalic acid diethylester-3,4-methylenedioxyphenylhydrazone (content: 95%) (91.7% of theoretical).

Fp: 71°–72° C.

|  | Elementary analysis: | | |
| --- | --- | --- | --- |
|  | C | H | N |
| calculated | 54.59% | 5.19% | 9.10% |
| found | 54.60% | 5.04% | 9.14% |
|  | 54.54% | 5.31% | 9.23% |

Analogously, from malonic acid dimethylester, the corresponding mesoxalic acid dimethylester-3,4-methylenedioxyphenylhydrazone is prepared (Yield: 89.3%).

Fp: 117°–123° C.

|  | Elementary analysis: | | |
| --- | --- | --- | --- |
|  | C | H | N |
| calculated | 51.43% | 4.32% | 9.99% |
| found | 51.57% | 4.44% | 9.81% |
|  | 51.40% | 4.30% | 9.79% |

EXAMPLE 2

In a 6 l sulfonation flask with stirrer and thermometer, 308 g mesoxalic acid diethylester-3,4-methylenedioxyphenylhydrazone are dissolved in a mixture of 0.5 l methylene chloride and 2 l ethanol at 40° C. 300 ml of 4N NaOH are added to the solution and stirred for 3 hours. The Na-salt of the mesoxalic acid monoethylester separates from the solution already after a short period of time. The mixture is cooled to 10°–15° C. and subsequently, under further cooling, reacted with 105 ml concentrated hydrochloric acid. The arising precipitation is sucked off and washed with water until neutral reaction, and subsequently dried at 50° C.

Yield: 245 g mesoxalic acid monoethylester-3,4-methylenedioxyphenylhydrazone (87.5% of theoretical amount).

Fp.: 156°–158° C. (ethanol).

|  | Elementary analysis: | | |
| --- | --- | --- | --- |
|  | C | H | N |
| calculated | 51.43% | 4.32% | 10.0% |
| found | 51.52% | 4.39% | 9.89% |

-continued

| Elementary analysis: | | |
|---|---|---|
| C | H | N |
| 51.58% | 4.21% | 10.11% |

Analogously, in a mixture of methylene chloride and methanol, mesoxalic acid monomethylester-3,4-methylenedioxyphenylhydrazone is produced. (Yield: 83%) mesoxalic acid monomethylester-3,4-methylenedioxyphenylhydrazone:

Fp: 177°–181° C. (methanol).

| | Elementary analysis: | | |
|---|---|---|---|
| | C | H | N |
| calculated | 49.63% | 3.79% | 10.52% |
| found | 49.67% | 3.78% | 10.24% |

EXAMPLE 3

In a 4 l sulfonation flask with stirrer, reflux cooler, drop funnel and thermometer, 750 ml xylene are heated to 95° C. 280 g mesoxalic acid monomethylester-3,4-methylenedioxyphenylhydrazone are added to the hot xylene, and the mixture is held at 90°–95° C. With strong stirring, 400 ml acetic anhydride and 120 ml phosphoroxychloride are added within 2 minutes. On the basis of the instituted exothermic reaction, the temperature rises to 105°–110° C. After the reaction dies off, which is recognized from the drop in temperature, the reaction mixture is stirred another 20 minutes at 95° C., and then the mixture is cooled to 20°–25° C. 100 ml water are added dropwise to the cooled mixture, slowly and under powerful stirring. In this connection, care must be taken that the temperature does not exceed 50° C. Then, a further 1.9 l water is added, and the mixture is stirred for 1 hour at 20° C. The precipitating crystallisate is sucked off and washed with 400 ml methylene chloride and then with water. The 6,7-methylenedioxy-4(1H)-oxo-cinnolin-3-carboxylic acid ethylester is dried at 70° C.

Yield: 155 g (59% of theoretical amount).
Fp: 262°–264° C. (ethanol).

| | Elementary analysis: | | |
|---|---|---|---|
| | C | H | N |
| calculated | 54.96% | 3.84% | 10.68% |
| found | 55.16% | 3.90% | 10.98% |
| | 55.22% | 3.74% | 11.16% |

UV: (ethanol) maxima at 246 nm, 345 nm and 359 nm.

EXAMPLE 4

In a 50 ml three-necked flask with reflux cooler and stirrer, 5.32 g mesoxalic acid monomethylester-3,4-methylenedioxyphenylhydrazone are added to a mixture of 16 ml acetanhydride and 2.2 ml phosphoroxychloride, and quickly heated to 95° C. under stirring. As a result of the instituted exothermic reaction, the temperature increases to 105° C. The temperature is then held for 10 minutes at 90°–100° C., and then the mixture is cooled to 80° C. The excess acetanhydride is extensively distilled off in a vacuum, and the viscous residue is reacted with 15 ml methylene chloride and 15 ml water, then stirred for 1 hour. The substance which crystallizes out is sucked off and then washed with 5 ml methylene chloride and 20 ml water.

Yield: 3.2 g (64.5% of theoretical amount): 6,7-methylenedioxy-4(1H)-oxo-cinnolin-3-carboxylic acid methylester.

Fp: 279°–282° C. (methanol).

| Elementary Analysis: MG: 257.2 $C_{11}H_8N_2O_5 \times \frac{1}{2} H_2O$ | | | |
|---|---|---|---|
| | C | H | N |
| calculated | 51.36% | 3.53% | 10.89% |
| found | 51.16% | 3.33% | 10.78% |
| | 51.21% | 3.27% | 10.89% |

EXAMPLE 5

28 g mesoxalic acid monoethylester-3,4-methylenedioxyphenylhydrazone are, in a mixture of 100 ml propionic acid anhydride and 11 ml phosphoroxychloride, quickly heated to 95° C. With the onset of reaction, there occurs a temperature increase to 102° C. Stirring is then performed for a further 30 minutes, and then the mixture is cast onto 500 g of crushed ice, under stirring. The somewhat oily substance is separated and mixed with 50 ml ethanol, until a well suction-removable yellow substance is produced. The product is sucked off and after-washed with a little ethanol.

Yield: 16 g 6,7-methylenedioxy-4(1H)-oxo-cinnolin-3-carboxylic acid ethylester (61% of theoretical amount).

EXAMPLE 6

A mixture of 2.8 g of mesoxalic acid monoethylester-3,4-methylenedioxyphenylhydrazone, 5 ml acetic anhydride and 5 g polyphosphoric acid ester (Synthesis 1979, 429) is stirred for 1 hour at 95° C. After cooling to room temperature, the mixture is cast onto ice and 15 ml acetic acid ethylester are added, followed by 15 minutes stirring. After standing for several hours, the separated product is sucked off, washed with water and dried.

Yield: 1.1 g 6,7-methylenedioxy-4(1H)-oxo-cinnolin-3-carboxylic acid ethylester (42%) of theoretical amount).

Fp: 260°–262° C. (ethanol).

IR and DC proved identical with an authentic sample.

EXAMPLE 7

2.8 g mesoxalic acid monoethylester-3,4-methylenedioxyphenylhydrazone, 1.6 g water-free sodium acetate, 1.6 g acetylchloride and 25 g polyphosphoric acid ester are stirred for 3 hours at 95° C. The reaction mixture is reacted with ice, the arising aqueous phase is decanted, and the semi-solid residue is reacted with acetone. 6,7-methylenedioxy-4(1H)-oxo-cinnolin-3-carboxylic acid ethylester crystallizes out.

Yield: 0.8 g (30.5% of theoretical amount).
Fp: 255°–257° C.

The substance is identical with an authentic sample, according to IR.

EXAMPLE 8

262 g 6,7-methylenedioxy-4(1H)-oxo-cinnolin-3-carboxylic acid ethylester and 110 g calc. sodium carbonate are suspended in 1.5 l dry dimethylformamide, and 150 ml ethyl bromide are added under stirring. The reaction mixture is heated for 3 hours to 70° C. under stirring, subsequently the dimethylformamide is distilled off in a vacuum, and the residue is withdrawn with 2 l methanol. To this solution, which is heated to 50° C., are added 60 g sodium hydroxide in 150 ml water, followed by 1 hour of stirring. After cooling to room temperature, the mixture is acidified with hydrochloric acid, the obtained precipitation is sucked off and washed neutral with water.

Yield: 250 g of a mixture of 1-ethyl-6,7-methylenedioxy-4(1H)-oxo-cinnolin-3-carboxylic acid and the anhydride base of 2-ethyl-6,7-methylenedioxy-4-hydroxy-cinnolinium-3-carboxylic acid in a ratio 85:15.

EXAMPLE 9

250 g of the substance obtained according to Example 8 are heated to 125° C. in 1.5 l dimethylformamide, and directly after obtaining this temperature cooled to below 100° C. The solution is condensed to 500 ml in a vacuum, and the crystallisate separating after the cooling is sucked off, washed with 200 ml dimethylformamide, and subsequently stirred for 1 hour with 2 l 5% sodium carbonate solution. The solution is filtered and subsequently acidified with hydrochloric acid to a pH of 1. The precipitated white substance is filtered, washed neutral with water and dried.

Yield: 207 g 1-ethyl-6,7-methylenedioxy-4(1H)-oxo-cinnolin-3-carboxylic acid (79% of theoretical amount). Fp: 266°–268° C.

|  | Elementary analysis: | | |
| --- | --- | --- | --- |
|  | C | H | N |
| calculated | 54.96% | 3.84% | 10.68% |
| found | 54.74% | 3.87% | 10.50% |
|  | 54.95% | 3.81% | 10.60% |

EXAMPLE 10

To a stirred suspension of 2.62 g 6,7-methylenedioxy-4(1H)-oxo-cinnolin-3-carboxylic acid ethylester, 2.8 g potassium carbonate, 1.4 g pulv. sodium hydroxide in 50 ml toluene, after addition of 0.4 g methyltrioctylammonium chloride, at 100° C. a solution of 1.52 ml ethylbromide in 5 ml toluene is added dropwise. After 2 hours and again after 3 hours, each time 0.76 ml ethyl bromide in 5 ml toluene are added dropwise. After a reaction period totalling 4 hours, the mixture is cooled to room temperature, 25 ml water are added, followed by 2 hours of stirring.

The aqueous phase is then separated, filtered and acidified with hydrochloric acid. There precipitates a crude substance of 1-ethyl-6,7-methylenedioxy-4(1H)-oxo-cinnolin-3-carboxylic acid with a content of 80%, which is further purified through re-precipitation.

Yield: 2.05 g.

It will be understood that each of the elements described above, or two or more together, may also find a useful application in other types of preparations differing from the types described above.

While the invention has been illustrated and described as embodied in a method for the production of 1-alkyl-6,7-methylenedioxy-4(1H)-oxo-cinnolin-3-carboxylic acids, it is not intended to be limited to the details set forth, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

We claim:

1. Method for the production of 1-alkyl-6,7-methylenedioxy-4(1H)-oxo-cinnolin-3-carboxylic acids of the formula V

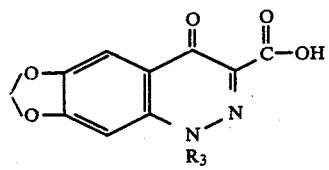

$R_3 = -CH_3; -C_2H_5; -C_3H_7; -C_4H_9$ comprising diazotization of 3,4-methylenedioxyaniline by means of sodium nitrite and mineral acid to form 3,4-methylenedioxyphenyldiazonium salt and coupling this with malonic acid dialkylester, thereby producing mesoxalic acid dialkylester-3,4-methylenedioxyphenylhydrazone of the formula I

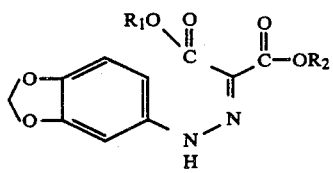

$R_1 = -CH_3; -C_2H_5; -C_3H_7; -C_4H_9$
$R_2 = -CH_3; -C_2H_5; -C_3H_7; -C_4H_9$ and isolating said compound of formula I, saponifying of one ester group of said compound of Formula I with 1 to 1.5 mol alkali, thereby producing monoalkylester of the Formula II

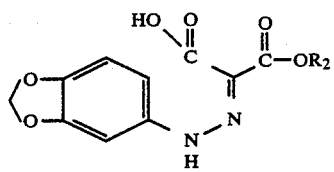

$R_2$ having the above-given meaning, isolating said compound of Formula II, reacting said compound of Formula II with a Friedel-Crafts catalyst selected from the group consisting of POCl₃, PCl₅ at 1–1.5 mol, excess of polyphosphoric acid and excess of polyphosphoric ester in the presence of a carboxylic acid anhydride into the 6,7-methylenedioxy-4(1H)-oxo-cinnolin-3-carboxylic acid alkylester of the Formula III

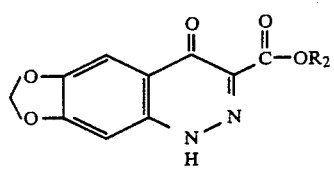

$R_2$ having the above-given meaning, separating the solid product and reacting said compound of Formula III with a C₁–C₄-alkyl halogenide in the presence of alkali in a solvent, to produce a compound of the formula IV

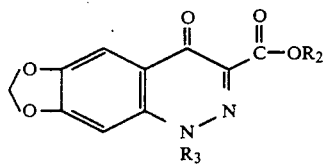

$R_2$ and $R_3$ having the above-given meaning, isolating said compound of Formula IV and saponifying of one ester group of said compound of Formula IV.

2. Method according to claim 1, using acetic anhydride or propionic acid anhydride as carboxylic acid anhydride.

3. Method according to claim 1, wherein the carboxylic acid anhydride is produced in situ during the reaction.

4. Method according to claim 1, wherein the reaction into the compound of Formula III is performed in a solvent.

5. Method according to claim 4, wherein said solvent is dichloroethane, toluene, benzene, xylene, chlorobenzene or nitrobenzene.

6. Method according to claim 1, wherein the alkylation is performed with $C_1$–$C_4$ alkylbromide in the presence of solid alkali.

7. Method according to claim 6, wherein said solid alkali is NaOH, $K_2CO_3$ or $Na_2CO_3$.

8. Method according to claim 1, wherein the alkylation is performed in the presence of a phase transfer catalyst.

9. Method according to claim 1, wherein the alkylation is performed in an organic solvent at temperatures between 30° and 100° C.

10. Method according to claim 9, wherein said organic solvent is toluene, benzene, methylene chloride, chloroform or dimethylformamide.

11. Method according to claim 1, wherein the saponification of the 1-alkyl-6,7-methylenedioxy-4(1H)-oxo-cinnolin-3-carboxylic acid alkylester of the general Formula IV is performed in a organic solvent at 20°–70° C. in the presence of alkali.

12. Method according to claim 11, wherein said organic solvent is an alcohol such as methanol or ethanol.

13. Method according to claim 1, further comprising after the second said saponifying, whereby a mixture results having predominantly 1-alkyl-6,7-methylenedioxy-4(1H)-oxo-cinnolin-3-carboxylic acid and small amounts of compound alkylated in the 2-position, removing said compound alkylated in the 2-position from said mixture by heating said mixture in a solvent to 100°–130° C., for 2–10 minutes, allowing a crystallisate to form, dissolving said crystallisate in aqueous alkali carbonate solution, filtering off any undissolved substance, and treating the solution with acid to precipitate pure 1-alkyl-6,7-methylenedioxy-4(1H)-oxo-cinnolin-3-carboxylic acid.

14. Method according to claim 13, wherein said solvent is dimethylformamide.

15. Method according to claim 13, wherein said heating is performed to 120° C.

* * * * *